United States Patent [19]

Kappel

[11] Patent Number: 5,640,727
[45] Date of Patent: Jun. 24, 1997

[54] CONTOURED INFLATABLE BLANKET

[75] Inventor: Thomas F. Kappel, St. Louis, Mo.

[73] Assignee: Mallinckrodt Medical, Inc., St. Louis, Mo.

[21] Appl. No.: 544,906

[22] Filed: Oct. 18, 1995

[51] Int. Cl.⁶ .................................................. A47G 9/02
[52] U.S. Cl. ...................... 5/482; 5/502; 5/423; 607/104
[58] Field of Search ................... 607/104; 5/502, 5/421, 423, 482; 62/259.3, 261; 126/204; 165/46

[56] References Cited

U.S. PATENT DOCUMENTS

| | | |
|---|---|---|
| 630,565 | 8/1899 | Safran . |
| 1,291,191 | 1/1919 | Semple . |
| 1,590,522 | 6/1926 | Kalman . |
| 1,777,982 | 10/1930 | Popp . |
| 2,093,834 | 9/1937 | Gaugler . |
| 2,110,022 | 3/1938 | Kliesrath . |
| 2,122,964 | 7/1938 | Sweetland . |
| 2,235,966 | 3/1941 | Summers . |
| 2,512,559 | 6/1950 | Williams . |
| 2,601,189 | 6/1952 | Wales, Jr. . |
| 2,617,915 | 11/1952 | Blair . |
| 2,700,165 | 1/1955 | Talisman . |
| 2,706,988 | 4/1955 | Weber . |
| 2,791,168 | 5/1957 | Mauch . |
| 2,834,033 | 5/1958 | O'Brien . |
| 2,998,817 | 9/1961 | Armstrong . |
| 3,034,132 | 5/1962 | Landsberger . |
| 3,307,554 | 3/1967 | Thornton . |
| 3,308,850 | 3/1967 | Gill . |
| 3,610,251 | 10/1971 | Sanderson . |
| 3,674,034 | 7/1972 | Hardy . |
| 3,740,777 | 6/1973 | Dee . |
| 3,757,366 | 9/1973 | Sacher . |
| 3,844,339 | 10/1974 | Kranz . |
| 4,026,299 | 5/1977 | Sauder . |
| 4,094,357 | 6/1978 | Sgroi . |
| 4,398,535 | 8/1983 | Guibert . |
| 4,457,295 | 7/1984 | Roehr . |
| 4,572,188 | 2/1986 | Augustine et al. . |
| 4,653,131 | 3/1987 | Diehl . |
| 4,660,388 | 4/1987 | Greene, Jr. . |
| 4,777,802 | 10/1988 | Feher . |
| 4,807,644 | 2/1989 | Sandhaus . |
| 4,867,230 | 9/1989 | Voss . |
| 4,959,877 | 10/1990 | Covil . |
| 4,997,230 | 3/1991 | Spitalnick . |
| 5,022,110 | 6/1991 | Stroh . |
| 5,044,364 | 9/1991 | Crowther . |
| 5,097,548 | 3/1992 | Heck et al. . |
| 5,106,373 | 4/1992 | Augustine et al. . |
| 5,125,238 | 6/1992 | Ragan et al. ............... 5/423 X |
| 5,165,400 | 11/1992 | Berke . |
| 5,184,612 | 2/1993 | Augustine . |
| 5,265,559 | 11/1993 | Stephenson et al. ............ 5/423 X |
| 5,265,599 | 11/1993 | Stephenson et al. . |
| 5,300,098 | 4/1994 | Philipot . |
| 5,300,100 | 4/1994 | Hickle et al. . |
| 5,300,101 | 4/1994 | Augustine et al. . |
| 5,300,102 | 4/1994 | Augustine et al. . |
| 5,304,213 | 4/1994 | Berke et al. ............... 607/104 |
| 5,304,217 | 4/1994 | Stephenson et al. . |
| 5,318,568 | 6/1994 | Kaufmann et al. . |

(List continued on next page.)

FOREIGN PATENT DOCUMENTS

| | | |
|---|---|---|
| 1325484 | 12/1993 | Canada . |
| 0311336 | 4/1989 | European Pat. Off. . |
| 149244 | 11/1931 | Switzerland . |
| 8503216 | 8/1985 | WIPO . |
| 9403131 | 2/1994 | WIPO . |
| 9520371 | 8/1995 | WIPO . |
| 9535077 | 12/1995 | WIPO . |
| 9603098 | 2/1996 | WIPO . |

Primary Examiner—Michael F. Trettel
Attorney, Agent, or Firm—Rothwell, Figg, Ernst & Kurz

[57] ABSTRACT

The present invention relates to blankets for use with forced air convection systems, wherein the blankets are sealed together at a plurality of spot welds and may be contoured for comfort and versatility. The contoured profile of the blanket is provided by varying the density pattern of the spot welds.

9 Claims, 3 Drawing Sheets

U.S. PATENT DOCUMENTS

| | | |
|---|---|---|
| 5,324,320 | 6/1994 | Augustine et al. . |
| 5,336,250 | 8/1994 | Augustine . |
| 5,343,579 | 9/1994 | Dickerhoff et al. . |
| 5,350,417 | 9/1994 | Augustine . |
| 5,360,439 | 11/1994 | Dickerhoff et al. . |
| 5,384,924 | 1/1995 | Dickerhoff et al. . |
| 5,392,847 | 2/1995 | Stephenson . |
| 5,405,370 | 4/1995 | Irani .......... 607/104 |
| 5,405,371 | 4/1995 | Augustine et al. . |
| 5,408,712 | 4/1995 | Brun . |
| 5,443,488 | 8/1995 | Namenye et al. . |

CONTOURED INFLATABLE BLANKET

BACKGROUND

Hypothermia is a condition of subnormal body temperature and presents serious consequences to the patient suffering therefrom. It has been shown that nearly seventy five percent of all patients who undergo surgical procedures develop hypothermia. This equates to approximately fourteen million patients a year in the United States alone. The hypothermic condition is brought on by many factors including anesthesia, the air conditioning of the operating room, and the infusion of cold blood, I-V solutions, or irrigating fluids.

Several methods and products have been developed to help prevent hypothermia from occurring; such as the use of infrared lamps, cotton blankets, and warm water mattresses. However, none of these methods and products have proven completely successful. In fact, it has been shown that these methods and products can not even prevent the patients from losing their endogenous heat. (See Journal of Post Anesthesia Nursing, Vol. 5, No. 4, August 1990, pp 254-263).

Another method of helping to prevent hypothermia that has proven very effective is the use of forced warm air convection. As early as 1937, a refrigeration blanket using cold air convection was suggested in U.S. Pat. No. 2,093,834 to Gaugler. This blanket included a plurality of layers for channeling airflow from an inlet port. Non-inflatable portions were provided around the periphery of the blanket to secure the blanket around the body.

U.S. Pat. No. 2,512,559 to Williams also relates to a blanket for providing cooled air to a person. The blanket in Williams comprised a plurality of thin sheets of material connected together at a plurality of discrete locations and connected together in a continuous line about the peripheral edge. An air inlet was provided to communicate with space between the sheets to allow cool air to be supplied thereto.

In U.S. Pat. No. 4,572,188 to Augustine, et al., a forced air convection system which can supply either cool or warm air to a blanket is described. The blanket in Augustine, et al. comprises a plurality of inflatable hollow tubes having their interiors connected together through transverse openings. An entry port is provided in the upper surface of the blanket for admitting the cool or warm air and small exit ports are provided through the lower surface to allow the cool or warm air to flow out toward a body covered by the blanket.

Other patents relating to the supply of cool or warm air to a person through an inflatable blanket include U.S. Pat. Nos. 4,660,388 to Greene, Jr.; 4,777,802 to Feher; and 4,867,230 to Voss; 5,125,238 to Ragan et al; 5,300,100 to Hickle et al; 5,300,102 to Augustine et al; 5,324,320 to Augustine et al; 5,343,579 to Dickerhoff et al; 5,360,439 to Dickerhoff et al; and 5,384,924 to Dickerhoff et al. Each of these patents describe blankets having various attributes and configurations to supply cool or warm air to the person.

While there are a number of patents noted above and others not mentioned which relate to inflatable blankets for use in supplying cool or warm air to a patient, there remains a need in the art for improvements to forced air convection systems.

OBJECTS OF THE INVENTION

It is one object of the present invention to provide a blanket for a forced air convection system which is contoured to fit the body of a patient.

SUMMARY OF THE INVENTION

The above objects and others are accomplished according to the present invention by providing a blanket for a forced air convective system having an upper material layer and a lower material layer connected together at a plurality of spot welds, wherein the spot weld pattern is varied in certain areas so as to create contoured areas of the blanket.

DETAILED DESCRIPTION OF THE INVENTION

Figure 1:
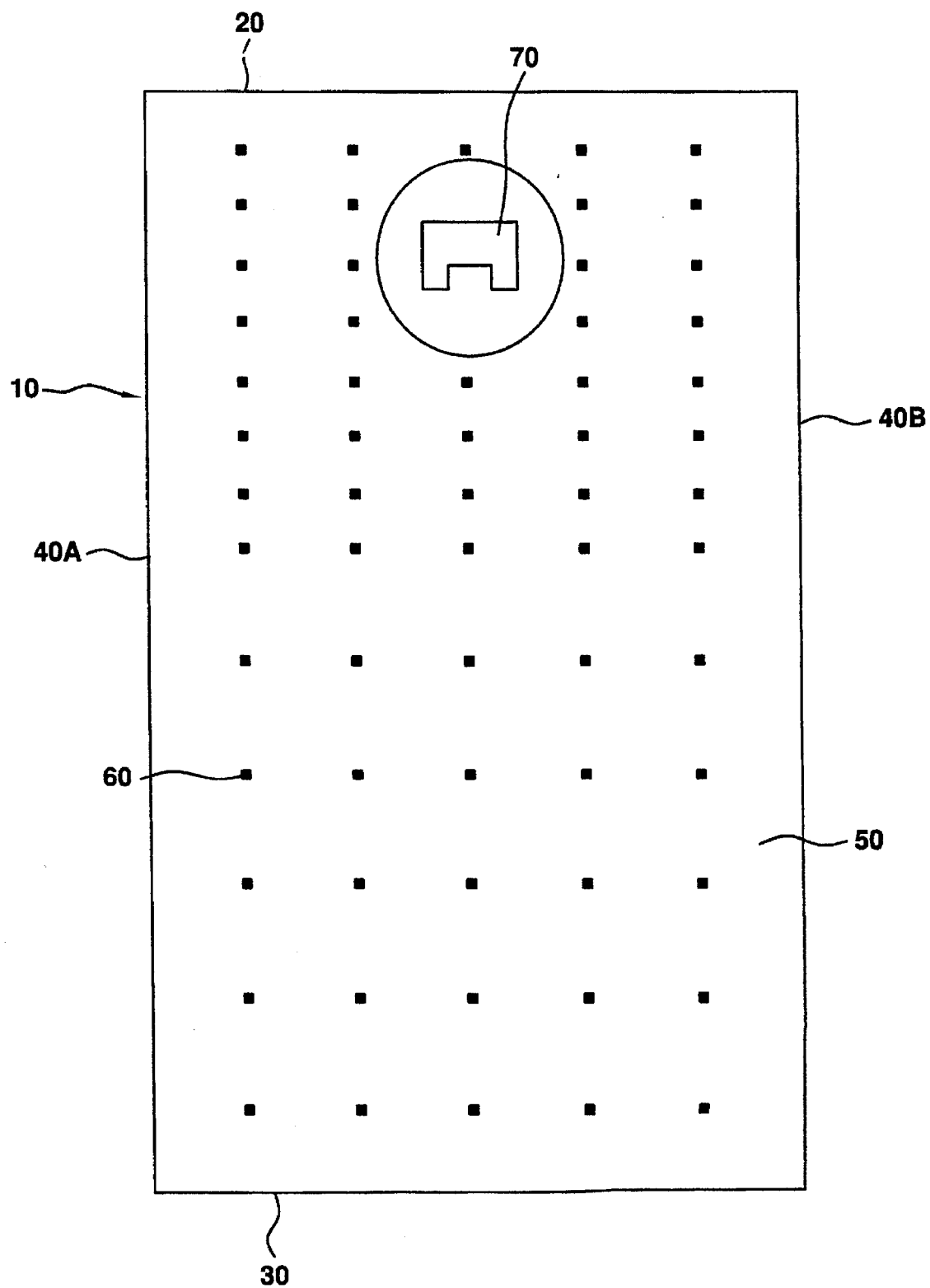
FIG. 1 is a plan view of a blanket for a forced air convection system according to one embodiment of the present invention.

FIG. 1 is a plan view of a blanket, generally designated by reference numeral 10, for a forced air convection system, according to one embodiment of the present invention. In particular, blanket 10, includes a head end 20, a foot end 30, and sides 40A, 40B. Blanket 10, further comprises a lower sheet of material (not visible), and an upper sheet of material 50, which are sealed together around respective peripheral edges to form an inflatable cavity therebetween. The lower sheet and upper sheet 50, are further sealed together at a plurality of spot welds 60, which produce a quilt-like pattern upon inflation of the blanket.

The blanket 10, includes at least one inlet port 70, for attachment to a source of forced air which will be used to inflate the blanket 10, and provide either warming or cooling air to the patient. As shown in FIG. 1, the inlet port 70, is formed through the surfaces of the blanket 10, at an interior location spaced away from the edges of the blanket 10. Other configurations are equally acceptable and are within the scope of the present invention. For example, the inlet port may be formed at a corner of the blanket 10, or along any edge of the blanket 10. In addition, multiple inlets may be provided for greater versatility to the user. The lower sheet of the blanket 10, preferably has a plurality of perforations or small exit holes formed therethrough which allow air to escape from the blanket 10, toward a patient.

As is apparent in FIG. 1, the welds 60, are provided in a pattern of varying density. In particular, the welds 60, are provided more densely toward the head end 20, of the blanket 10. By varying the density of the welds 60, the blanket 10, is provided with a contoured profile, wherein the blanket 10, will have a thinner profile upon inflation in those areas where the welds 60, are more densely provided. This aspect of the present invention will be explained in greater detail below with reference to FIGS. 2 and 3.

Figure 2A:
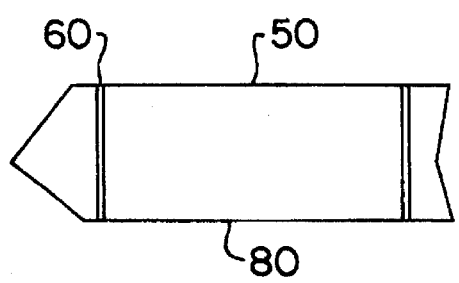
FIG. 2A is a cross-sectional view of a portion of a blanket according to the present invention in a non-inflated state, showing welds spaced relatively far apart.
Figure 2B:
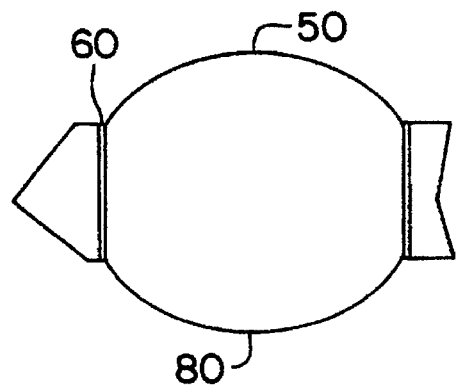
FIG. 2B is a cross-sectional view of the blanket shown in FIG. 2A, shown in an inflated state.

FIG. 2A is a cross-sectional view of a portion of a blanket in a non-inflated state wherein the welds 60, are spaced relatively far apart. In particular, FIG. 2A shows the upper sheet 50, the lower sheet 80, and two welds 60. FIG. 2B is a cross-sectional view of the blanket shown in FIG. 2A, but now shown in an inflated state. As is apparent, upon inflation the upper sheet 50, and lower sheet 80, both balloon outward from the welds 60. In the embodiment shown in FIGS. 2A and 2B, the inflated profile of the blanket is at maximum thickness.

Figure 3A:
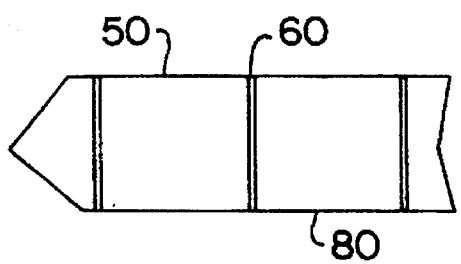
FIG. 3A is a cross-sectional view of a portion of a blanket according to the present invention in a non-inflated state, showing welds are spaced relatively close together.
Figure 3B:
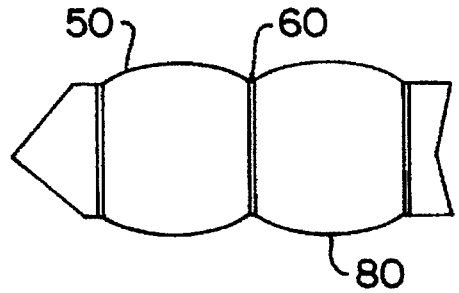
FIG. 3B is a cross-sectional view of the blanket shown in FIG. 3A, shown in an inflated state.

FIG. 3A is a cross-sectional view of a portion of a blanket in a non-inflated state wherein the welds 60, are spaced relatively close together. In particular, FIG. 3A shows the upper sheet 50, the lower sheet 80, and three welds 60. FIG. 3B is a cross-sectional view of the blanket shown in FIG. 3A, but now shown in an inflated state. As is apparent, upon inflation the upper sheet 50, and lower sheet 80, both balloon outward from the welds 60. In the embodiment shown in FIGS. 3A and 3B, the inflated profile of the blanket is at a reduced thickness.

In accordance with the present invention, the inflated profile of the blanket in areas where welds are spaced close to each other, is less than the inflated profile of the blanket where welds are spaced further apart. Therefore, by varying the distance between welds, and thus the density of the weld pattern, the contour of the blanket can be altered and controlled. In the embodiment shown in FIG. 1, the welds 60, are spaced closer together at the head end 20, of the blanket 10. In this manner, the inflated profile of the blanket 10, is thinner in the head end 20, which provides several advantages. For example, having a thinner blanket profile near the head end provides for less billowing around the head and face of the patient, which in turn provides the medical team with better viewing and access of the patient. Further, the blanket is more comfortable for the patient because it does not protrude into or over the face of the patient.

Figure 4:
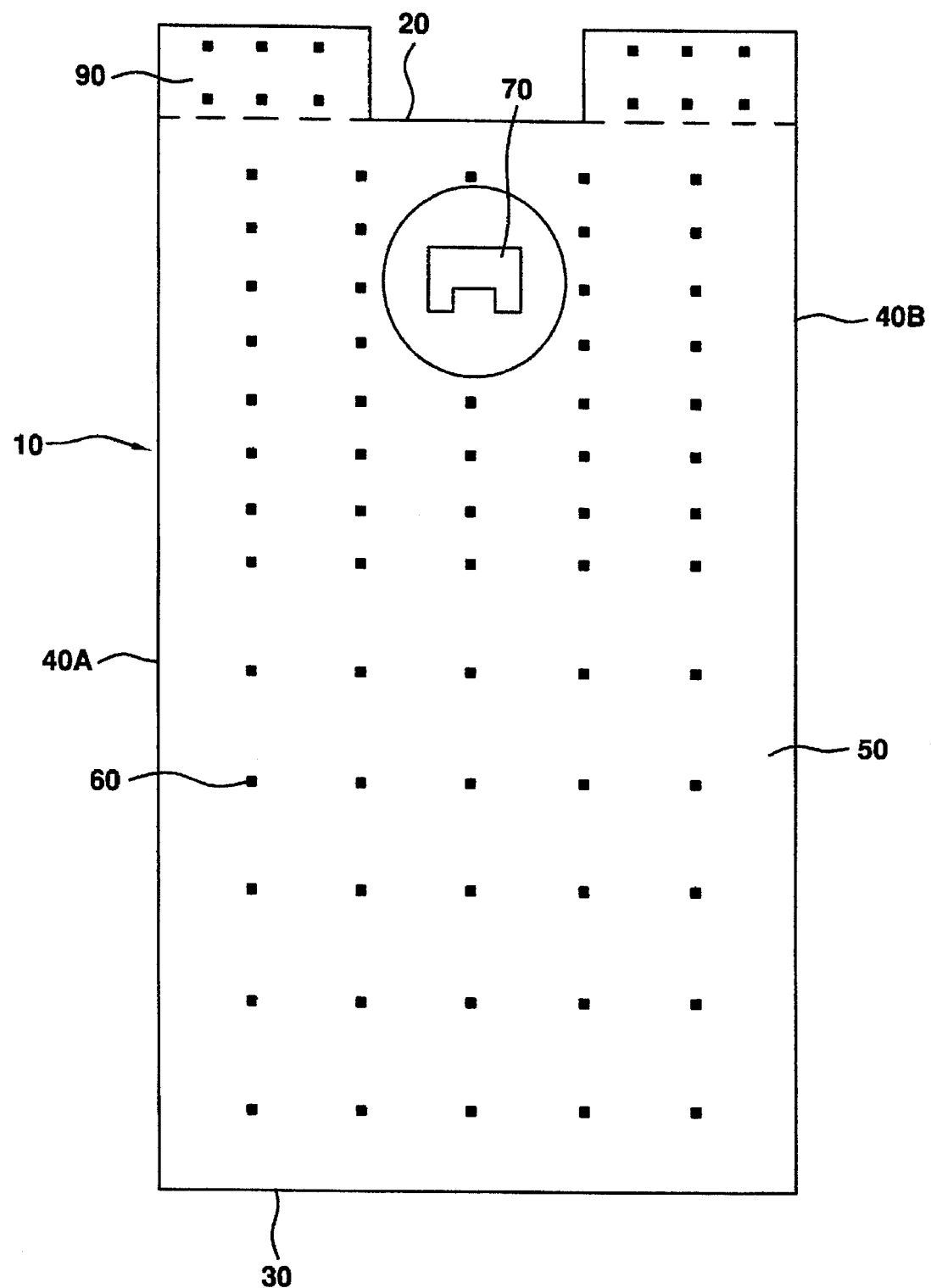
FIG. 4 is a plan view of a blanket for a forced air convection system according to a further embodiment of the present invention.

In a preferred embodiment, shown in FIG. 4, the blanket 10, is reduced in contour toward the head end 20, and is also provided with shoulder extensions 90, which can be tucked around and under the patient's shoulders, to help stabilize the blanket 10, during use. The shoulder extensions 90, may be either inflatable or non-inflatable sections of the blanket 10, but in any case will have relatively densely packed welds 60, to facilitate their use.

The present invention also relates to any number of desired contour patterns which may be provided by varying the density pattern of the welds. As noted with reference to FIG. 1, the blanket 10, may be contoured near the head end 20. However, the blanket could be contoured near the foot end, or along the edges, or portions thereof. Further, the blanket could be provided with multiple contoured sections.

The present invention also relates to blankets having gradual or varying contours. In particular, the inflated profile of the blanket can be controlled by varying the density pattern of the welds. The closer the welds, the thinner the inflated profile as demonstrated in FIGS. 2 and 3. By varying the distance between the welds, a tapered contour can be achieved. In addition, dips, or hollows can be formed across the surface of the blanket if so desired. If multiple contours are to be provided, such can be done in different patterns to achieve different inflation profiles in different areas of the blanket. Moreover, the distance between the welds in the longitudinal direction may be symmetrical with the distance between welds in the horizontal direction to provide a evenly contoured blanket. Conversely, the distance between welds in the longitudinal direction may be different than the distance between welds in the horizontal direction to provide a contour in only one direction, or to provide different contours in different directions.

The blanket shown in FIGS. 1 represent full body-blankets but the present invention would be equally applicable to blankets intended to cover only portions of the patient, such as an upper body blanket or a lower body blanket. The blankets according to the present invention are also equally useful in both adult and pediatric sizes. The blankets above may be used equally effectively in either the operating room, or in other areas of the hospital, such as the PACU. Moreover, as noted, the blankets according to the present invention may be used to provide either warming or cooling to a patient.

The blankets of the present invention may be formed of any suitable material capable of being sealed together at selected positions and having sufficient strength to allow inflation and adequate air distribution within the inflated portion. Such materials include plastics, non-woven wood pulp compositions, laminated plastic and wood pulp materials, and combinations thereof.

The foregoing has been a description of certain preferred embodiments of the present invention, but is not intended to limit the invention in any way. Rather, many modifications, variations and changes in details may be made within the scope of the present invention.

What is claimed is:

1. An inflatable blanket for a forced air convection system comprising:

an upper sheet of material having a generally rectangular shape with a head end, a foot end and two sides;

a lower sheet of material having a generally rectangular shape with a head end, a foot end and two sides;

wherein said upper sheet and said lower sheet are sealed together around their peripheral edges at their respective head ends, foot ends and sides, to create an inflatable blanket with a cavity having a head end, a foot end, and two sides therebetween;

wherein said upper sheet and said lower sheet are further sealed together across their respective surfaces at a plurality of spot welds;

an inflation port connecting said inflatable cavity with the atmosphere and through which inflation medium may be introduced to said inflatable cavity to inflate said blanket;

wherein the density of said spot welds is varied in certain areas of said blanket to provide a contoured inflation profile, said spot welds having a pattern selected from the group consisting of:

a pattern wherein a distance between adjacent spot welds at the head end of the blanket is less than the distance between adjacent spot welds at said foot end of the blanket, so that said head end of the blanket has a thinner profile when inflated than said foot end of the blanket, a pattern wherein a distance between adjacent spot welds at said foot end of the blanket is less than the distance between adjacent spot welds at said head end of the blanket, so that said foot end of the blanket has a thinner profile when inflated than said head end of the blanket, and a pattern wherein distance between adjacent spot welds at one side of the blanket is less than the distance between adjacent spot welds at the other side of said blanket, so that said one side of the blanket has a thinner profile when inflated than said other side of the blanket.

2. A blanket according to claim 1, wherein said spot welds are provided more densely at said head end of said blanket.

3. A blanket according to claim 1, wherein said spot welds are provided more densely at said foot end of said blanket.

4. A blanket according to claim 1, wherein said spot welds are provided more densely along said one side of said blanket.

5. A blanket according to claim 1, wherein said spot welds are provided in a gradually increasing density pattern toward said one side of said blanket.

6. A blanket according to claim 5, wherein said spot welds are provided in a gradually increasing density pattern toward said head end of said blanket.

7. A blanket according to claim 1, wherein the density of said spot welds is greater in a longitudinal direction along said blanket than in a horizontal direction along said blanket.

8. A blanket according to claim 1, wherein the density of said spot welds is greater in a horizontal direction along said blanket than in a longitudinal direction along said blanket.

9. A blanket according to claim 1, wherein blanket further includes shoulder extensions extending from said head end which may be tucked under a patient's shoulders when said blanket is in use.

* * * * *

UNITED STATES PATENT AND TRADEMARK OFFICE
Certificate

Patent No. 5,640,727                                                           Patented: June 24, 1997

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Thomas F. Kappel, St. Louis, Missouri; Scott D. Dickerhoff, Manchester, Missouri; and Dennis S. Chivetta, Ballwin, Missouri.

Signed and Sealed this Ninth Day of April 2002.

JACK W. LAVINDER
*Supervisory Patent Examiner*
Art Unit 3628

UNITED STATES PATENT AND TRADEMARK OFFICE
CERTIFICATE OF CORRECTION

PATENT NO.  : 5,640,727
DATED       : June 24, 1997
INVENTOR(S) : Thomas F. Kappel, Scott D. Dickerhoff and Dennis S. Chivetta It is certified that error appears in the above-identified patent and that said Letters Patent is hereby corrected as shown below:

Title page,
Item [75], Inventors, please correct inventorship to read -- Thomas F. Kappel, St. Louis, Missouri; Scott D. Dickerhoff, Manchester, Missouri; Dennis S. Chivetta, Ballwin, Missouri --.

Signed and Sealed this

Twenty-third Day of April, 2002

Attest:

JAMES E. ROGAN
Director of the United States Patent and Trademark Office

*Attesting Officer*